United States Patent [19]

Coope et al.

[11] Patent Number: 5,393,902
[45] Date of Patent: Feb. 28, 1995

[54] PROCESS FOR THE PREPARATION OF BIS(AMIDOCARBOXYLIC ACIDS)

[75] Inventors: Janet L. Coope, Hackensack; AnneMarie Brescia, Fairview; Michael I. Hill, Ridgewood; Martina Santoso, North Brunswick, all of N.J.; Stephen A. Madison, New City, N.Y.

[73] Assignee: Lever Brothers Company, Division of Conopco, Inc., New York, N.Y.

[21] Appl. No.: 233,165

[22] Filed: Apr. 26, 1994

[51] Int. Cl.$^6$ .................. C07C 231/02; C07C 229/24; C07C 61/08
[52] U.S. Cl. ..................... 554/69; 554/104; 562/507; 562/458; 562/457; 562/450; 562/565
[58] Field of Search ............... 562/457, 565, 450, 458, 562/507; 554/69, 104

[56] References Cited

U.S. PATENT DOCUMENTS

| | | | |
|---|---|---|---|
| 3,296,303 | 1/1967 | Nemec. | |
| 4,634,551 | 1/1987 | Burns et al. | 252/102 |
| 4,686,063 | 8/1987 | Burns | 252/102 |
| 5,061,807 | 10/1991 | Gethoffer et al. | 548/473 |
| 5,132,431 | 7/1992 | Fuchs et al. | 548/473 |

FOREIGN PATENT DOCUMENTS

| | | |
|---|---|---|
| 0445096 | 9/1991 | European Pat. Off. . |
| 949568 | 9/1956 | Germany . |
| 159285 | 4/1987 | India . |

OTHER PUBLICATIONS

Chemical Abstract 81(7):37257n Apr. (1974).
JP 47027955 Oct. 30, 1972.
Makromol. Chem. 1897(2) 401–10 (1986).
J. Amer. Oil Chemist Soc. 39, pp. 213–215 (1962).
J. Prakt. Chem. 17, pp. 147–153 (1962).
WO 90/14336 Nov. 1990.
WO 92/06073 Apr. 1992.

*Primary Examiner*—José G. Dees
*Assistant Examiner*—Joseph M. Conrad
*Attorney, Agent, or Firm*—Milton L. Honig

[57] ABSTRACT

A process is reported for the preparation of bis-(amidocarboxylic acid) involving reacting an ester with an aminocarboxylate compound, the latter being formed from lactams or aminocarboxylic acids and salts thereof. The ester and aminocarboxylate compound are present in a weight ratio of about 1:1 to about 1:4, and reaction is conducted in a mono- or polyhydric alcohol solvent.

12 Claims, No Drawings

PROCESS FOR THE PREPARATION OF BIS(AMIDOCARBOXYLIC ACIDS)

BACKGROUND OF THE INVENTION

1. Field of the Invention

The invention relates to a process for preparing bis(amidocarboxylic acids) which are key intermediates in the synthesis of bis(amidoperoxycarboxylic acid) bleaches.

2. The Related Art

Peroxyacids have long been known for their excellent fabric bleaching activity. More recently, amido peroxycarboxylic acids have been identified as particularly desirable because of their good stability in detergent compositions.

U.S. Pat. No. 4,634,551 (Burns et al) and U.S. Pat. No. 4,686,063 (Burns) describe peroxyacids having polar amide links along a hydrophobic backbone. All of the reported substances are monoperoxycarboxylic acids. U.S. Pat. No. 5,061,807 (Gethoffer et al) and U.S. Pat. No. 5,132,431 (Fuchs et al) describe a series of imido peroxyacids, chief among which is N-phthaloylaminoperoxycaproic acid (PAP). See also the related technology in EP 0 347 724 (Ausimont).

Bis(amidoperoxycarboxylic acids) have been disclosed in WO 90/14336 (Interox) which especially describes N,N'-terephthaloyl-di(6-aminoperoxycaproic acid), known as TPCAP. The exceptional stability of TPCAP, and related compounds, has occasioned the need for an improved synthesis. A necessary link in this synthesis is a route to the intermediate N,N'-terephthaloyl-di(6-aminocaproic acid) known as TOCAP.

The literature has described various methods for preparation of TOCAP and related compounds. German Patent 949,568 (Kruckenberg) discloses the reaction of caprolactam with various acyl halides including adipoyl dichloride in the presence of sodium hydroxide. Once sodium 6-aminocaproate has formed, the reactor is charged with a first portion acyl halide, sodium hydroxide and then a final portion acyl halide. A related method is reported by Zinner et al in *J. Prakt. Chem.* 17, 147-153 (1962). The procedure requires the addition of all the sodium hydroxide to be charged to the reaction vessel at the beginning of the synthesis. The reported yield is 70% of theory.

The problem with the aforementioned synthetic routes is that the yields are insufficiently high for commercial purposes. Secondly, these syntheses result in substantial amounts of undesirable by-products, especially the monoamide addition by-product. These by-products can lead to thermal instability and impact sensitivity in any eventual peracid formed therefrom.

A recent co-pending U.S. patent application Ser. No. 08/152,041, filed Nov. 12, 1993 describes a substantially improved method for obtaining TOCAP through the acid chloride route. Therein, an acyl halide is reacted with an amino carboxylate. Condensation is performed in water with sodium hydroxide as catalyst. Excellent yields and minimization of undesirable by-products are achieved by controlling pH between 10 and 14 during the condensation reaction.

Unfortunately no matter how efficient the acyl halide route, there remain certain inherent flaws in this synthetic strategy. Acyl halides are expensive reagents. These materials are not readily commercially available. More economical reagents are required. Since condensation routes using acid chlorides generate a chloride waste stream, there are environmental problems requiring extra engineering and waste disposal. Perhaps the most significant drawback to this process is the generation of chloride ion. Even small amounts of chloride ion will, under peroxidation, convert to hypochlorite, the latter interfering in conversion of TOCAP to TPCAP.

Accordingly, it is an object of the present invention to provide an improved synthesis of bis(amidocarboxylic acids).

Another object of the present invention is to provide a route to bis(amidocarboxylic acids) that achieves high yields.

A further object of the present invention is to provide a route to bis(amidocarboxylic acid) in which undesirable by-products are minimized.

A still further object of the present invention is to provide a route to bis(amidocarboxylic acid) through an environmentally friendly procedure wherein product cleanly and with minimal workup separates from the reaction medium.

Yet a further object of the present invention is to provide a route to bis(amidocarboxylic acid) which avoids contamination by chloride ion.

Still another object of the present invention is to provide a route to bis(amidocarboxylic acid) wherein the amino carboxylate reagent is prepared in a procedure that minimizes water content and need not be isolated from its solvent prior to further reaction.

Yet another object of the present invention is to provide a bis(amidocarboxylic acid) through a procedure that maximizes crystal size of recovered product.

These and other objects of the present invention will become more readily apparent through consideration of the following summary, detailed description and examples.

SUMMARY OF THE INVENTION

A process is provided for the preparation of a bis(amidocarboxylic acid) having the formula:

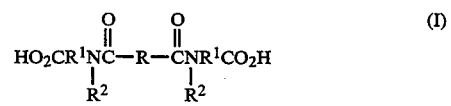

wherein

R and $R^1$ are each independently a $C_1$-$C_{12}$ radical selected from the group consisting of alkylene, alkenylene, cycloalkylene, cycloalkenylene, arylene and phenylene radicals; and $R^2$ is hydrogen or a $C_1$-$C_{12}$ radical selected from the group consisting of alkyl, alkenyl, cycloalkyl, cycloalkenyl, aryl and phenyl radicals;

the process comprising the steps of:

(i) charging a reactor with a reaction medium that includes a $C_1$-$C_8$ mono- or polyhydric alcohol as solvent, an ester and an aminocarboxylate compound, the ester having the formula:

wherein $R^3$ is a $C_1$-$C_6$ radical selected from the group consisting of alkyl, haloalkyl, hydroxyalkyl or phenyl radicals, the aminocarboxylate compound being a salt formed from and selected from the group consisting of lactams having the formula:

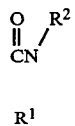
(III)

and aminocarboxylic acids having the formula:

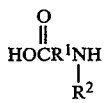
(IV)

the ester and aminocarboxylate compound being present in a respective weight ratio of from about 1:1 to about 1:4;

(ii) reacting the ester with the aminocarboxylate compound; and (iii) recovering the bis(amidocarboxylic acid) from the reaction medium.

DETAILED DESCRIPTION

A successful route to bis(amidocarboxylic acid) has now been found through an ester amidation procedure. High yields and excellent purity are achieved.

Typical industrial processes for amide synthesis from esters involve melt conditions. Therein, the ester and amine are heated to temperatures of 140° C. or higher. For example, EP 445 096 (Vanderlinde) prepares N-nonylamide methyl adipate through heating dimethyl adipate with nonylamine at 140° C. for two hours. Alkylolamides, such as lauric diethanolamide, are also prepared as a melt using sodium methoxide or potassium hydroxide catalysts as described in *J. Amer. Oil Chemist Soc.*, 39, 213 (1962). Unlike the aforementioned materials, alkylamino acids such as 6-aminocaproic acid under melt conditions (to 210° C.) self-polymerize. The problem arises from the bi-functionality of the amine reactant and the lack of selectivity between the carboxylic acid of the amine and the ester. Yields of 30% bis(amidocarboxylic acid) are accompanied by at least 40% polymer. These problems have been overcome through the present invention.

Accordingly, in its broadest aspect, the invention provides a process for the preparation of bis(amidocarboxylic acid) having the formula:

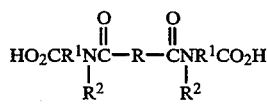
(I)

wherein

R and $R^1$ are each independently a $C_1$–$C_2$ radical selected from the group consisting of alkylene, alkenylene, cycloalkylene, cycloalkenylene, arylene and phenylene radicals; and $R^2$ is hydrogen or a $C_1$–$C_{12}$ radical selected from the group consisting of alkyl, alkenyl, cycloalkyl, cycloalkenyl, aryl and phenyl radicals.

There are two key reactants to the process of this invention. The first is an ester having the formula:

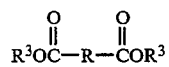
(II)

wherein $R^3$ is a $C_1$–$C_6$ radical selected from the group consisting of alkyl, haloalkyl, hydroxyalkyl and phenyl radicals.

The following esters are representative of the present invention.
dimethylterephthalate
diethylterephthalate
diisopropylterephthalate
dibutylterephthalate
diphenylterephthalate
dimethylsuccinate
diethylsuccinate
diisopropyladipate
dimethyladipate
dimethyldodecanedioate
dimethylsebacate
diphenylsebacate
dimethyl-trans- 1,4-cyclohexanedicarboxylate
dimethyl-trans- 1,2-cyclobutanedicarboxylate
di(2,2,2-trichloroethyl) terephthalate
di(2,2,2-trifluoroethyl) terephthalate
di(2-hydroxyethyl) terephthalate
Most preferred is dimethylterephthalate.

The second essential reactant of the present invention is that of an aminocarboxylate compound. The compound may be either an acid or salt, with the latter being preferred. When in salt form, the cation may be selected from the group consisting of alkali metal, alkaline earth metal, transition metal or ammonium ions. Most preferred are sodium salts. The compound may be formed from hydrolysis of a lactam (III) or from an aminocarboxylic acid (IV), and salts thereof obtained from reaction with a suitable base.

(III)

and

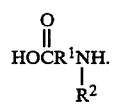
(IV)

The following aminocarboxylate compounds are representative of the present invention.

| LACTAMS | AMINOCARBOXYLIC ACIDS |
|---|---|
| ε-caprolactam | 6-aminocaproic acid |
| N-methyl caprolactam | 4-aminobenzoic acid |
| δ-valerolactam | 2-aminobenzoic acid |
| α-butyrolactam (2-pyrrolidone) | 3-aminopropionic acid |
| | 4-aminobutyric acid |
| | N-methyl-6-aminohexanoic acid |
| | N-ethyl-3-aminopropionic acid |
| | N-methyl-4-aminobenzoic acid |
| | 4-amino-cyclohexanoic acid |
| | glycine |
| | alanine |
| | valine |
| | leucine |
| | phenyl alanine |

| LACTAMS | AMINOCARBOXYLIC ACIDS |
|---|---|
| | lysine |

The base may be selected from the group consisting of $C_1$–$C_8$ alkoxides (e.g. sodium methoxide or ethoxide), sodium hydroxide, lithium hydroxide, calcium hydroxide, magnesium hydroxide, potassium hydroxide, sodium carbonate, lithium carbonate, potassium carbonate, tetrasodium pyrophosphate and trisodium phosphate. Most preferred are sodium methoxide and sodium hydroxide, the latter of which may be employed in concentrations of 10–50% in water or as pellets. The molar amount of base relative to the lactam (111) or aminocarboxylic acid (IV) will be from about 3:1 to about 1:3, preferably about 1:1.

The molar amount by weight of ester relative to aminocarboxylate compound will range from about 1:1 to about 1:4, preferably from about 1:2 to about 1:3.

Advantageously, the aminocarboxylate compound is a sodium salt prepared from a lactam. An alkali such as sodium methoxide or sodium hydroxide in alcohol opens the lactam ring to provide respectively an aminocarboxylate ester or salt. This alkali/solvent system when applied to ε-caprolactam provides sodium aminocaproate in high yield. Removal of alcohol solvent is unnecessary because the solution can directly be used as a medium for ester amidation. Good yields of bis(amidocarboxylic acid) are achieved. Alternatively ε-caprolactam is treated with alkali in aqueous solvent, the water being displaced by alcohol prior to introduction of the ester reactant.

Critical to the invention is use of a $C_1$–$C_8$ monohydric or polyhydric alcohol as solvent for the reaction. Suitable solvents include methanol, ethanol, isopropanol, n-propanol, phenol, ethylene glycol, glycerol, propylene glycol, 1,4-butanediol and diethylene glycol. Preferred solvents are methanol and ethylene glycol. In particular, certain advantages accrue with ethylene glycol. Ordinarily, no other solvent than these alcohols will be present in the reaction medium. Amounts of solvent to ester may range from about 500:1 to about 1:10, preferably from about 20:1 to 1:1 by weight. Water is best excluded to prevent hydrolysis of the ester competing with the amidation. Water should be present in no more than 2%, preferably no more than 0.1% by weight of the solvent system.

Generally, the reaction between the aminocarboxylate compound and the ester will be catalyzed by a base. Suitable bases include the alkalimetal salts of $C_1$–$C_8$ alkoxides, carbonates, pyrophosphates and aminocarboxylate compounds (i.e. the reactants). Amounts of the base catalyst relative to the ester will range from about 1:1 to about 1:1000, preferably from about 1:2 to about 1:20, optimally from about 1:3 to about 1:10, by weight.

Although not to be bound by theory, it is believed necessary to have a solvent that dissolves both the amino carboxylate salt (polar material) and the ester (non-polar material). Alcohols, especially methanol and ethylene glycol, were found to have properties particularly suitable for this purpose.

Crystal size of the resultant bis(amidocarboxylic acid) assumes importance when separating this material from a solvent at the end of the reaction. Upon completion of amidation in a monohydric alcohol solvent such as methanol, it has been found advantageous to maintain a water alcohol ratio of about 1:4 to 1:0.5, preferably 1:1, and then to acidify the medium to precipitate product. Acidification should be to a pH no lower than 4, i.e. a pH range from about 4 to about 6. Acidification in the alcohol/water solvent provides a sufficiently large particle size upon precipitation of product to allow easy separation of product from the mother liquor.

Amidation temperatures of the reaction may range from about 20° C. to about 200° C., but preferably range from about 30° C. to about 150° C., optimally from about 50° C. to about 135° C.

The following Examples will more fully illustrate the embodiments of this invention. All parts, percentages and proportions referred to herein and in the appended claims are by weight unless otherwise noted.

EXAMPLE 1

Synthesis of TOCAP From Caprolactam in Methanol

An autoclave containing a stir bar and caprolactam (11.34 g, 0.1002 mol) was charged with a solution of sodium hydroxide (4.01 g, 0.1002 mol) in anhydrous methanol (20 mL). The concentration was 5.0M. The autoclave was sealed and heated in a 140° C. oil bath; a pressure of 70 psi was generated by heating the reaction. After 22 hours, NMR spectra showed 99+% opening of caprolactam to sodium 6-aminocaproate. The sodium 6-aminocaproate (3 equiv.) in methanol, an off-white semi-solid, was transferred using additional methanol to a 250 mL 3-necked round bottomed flask equipped with overhead stirrer. Sodium methoxide solution (15.27 mL of 25 wt % in methanol, 0.0668 mol, 2 equiv.) and additional methanol were added to make a total volume of 133.6 mL methanol. Dimethyl terephthalate (6.48 g, 0.0334 mol, 1 equiv.) was added and the reaction brought to reflux. The reaction concentration was 0.25M in dimethyl terephthalate. After 5 minutes at reflux, the reaction mixture turned cloudy and became progressively thicker over the course of the reaction. After 18 hours, the reaction mixture was rinsed out of the flask with water and poured onto ice, water and sulfuric acid; pH was then brought to 1. The product was isolated by filtration and washed with water to give a white powder (10.4 g); purity by HPLC-75% TOCAP, 14% monoaddition acid, 0.3% terephthalic acid; TOCAP yield 59%.

EXAMPLE 2

Synthesis of TOCAP from Sodium 6-Aminocaproate in Ethylene Glycol

Into a 2L glass vessel were placed 6-aminocaproic acid (85.1 g, 0.65 mol), dimethylterephthalate (62.1 g, 0.32 mol) and ethylene glycol (400 mL). The mixture was stirred while 25 wt % sodium methoxide in methanol solution (166 g, 0.77 mol. $NaOCH_3$) was introduced slowly. The reactor was brought to 75° C. and held at this temperture for 24 hours. The temperature was lowered to 15° C. and 400 mL of water were slowly added to give a clear solution. Sulfuric acid solution (4.5M) was then added until a pH of 5 was achieved. The resulting white solid was collected by filtration and washed with water to provide 122 g of solid after drying. Purity was 89% giving a TOCAP yield of 85%.

EXAMPLE 3

Synthesis of TOCAP from Caprolactam in Ethylene Glycol

A 250 ml three-necked round-bottomed flask equipped with overhead stirring apparatus, shortpath distillation head and receiving flask, was charged with ground sodium hydroxide (4.02 g, 0.1004 mol), caprolactam (11.26 g, 0.1004 mol) and ethylene glycol (20 mL). The concentration was 5.0M in caprolactam. The reaction was heated and when the oil bath reached 110° C., 4 mL toluene were added to remove water azeotropically. Heating was continued at 136° C. for 24 hours. NMR spectra showed 98% opening of caprolactam to sodium 6-aminocaproate and the reaction was allowed to cool. To the reaction mixture were added additional ethylene glycol (39 mL), dimethyl terephthalate (9.28 g, 0.0478 mol) and sodium methoxide solution (4.132 g of 25 wt % in methanol, 0.0192 mol, 0.4 equiv.). The concentration was 0.81M in dimethyl terephthalate. After 24 hours at an internal temperature of 80° C., the mixture was poured onto ice, water and sulfuric acid; pH was then brought to 2. The product was isolated by filtration and washed with water to give 15.25 g; purity by HPLC- 58% TOCAP; TOCAP yield 47%.

EXAMPLE 4

Synthesis of TOCAP From Diphenylterephthalate

Preparation of TOCAP (Salt)

A 25 ml reaction flask, equipped with a mechanical stirrer, was charged with diphenylterephthalate (2.50 g, 7.85 mmol) and 2.1 equiv. of sodium 6-aminocaproate (2.54 g, 16.49 mmol). Phenol (16.82 g, 15.70 mL) was added as a liquid to give a 0.5M concentration of diphenylterephthalate. The stirred reaction mixture was heated at 70° C. via an oil bath and after 1 hour the solids were completely dissolved. After 22 hours, the solution was allowed to cool slightly, then ethyl ether was added. The resulting precipitate was collected and washed with additional ether. The material was dried under vacuum at 60° C. for 2 hours to give 3.39 g of a light-brown solid. HPLC analysis indicated 89% TOCAP sodium salt. Yield: 89%.

$^1$NMR (200MHz, D$_2$O): $\delta$7.81 (s, 4H), 3.41 (t, 4H, J=6.8 Hz), 2.21 (t, 4H, J=7.3 Hz), 1.70–1.40 (m 12H)

IR (Nujol): 3300, 1645, 1570, 1470, 1325, 1170, 870 cm$^{-1}$

Preparation of TOCAP (Acid)

The TOCAP salt (3.31 g, 7.6 mmol), as prepared above, was dissolved in about 50 50 mL of water and the solution cooled via an ice/water bath. A 1N solution of sulfuric acid was added and the pH adjusted to 4. The resulting precipitate was collected and washed with water. Upon vacuum drying at 70° C. for 5 hours, 2.36 g of a light-brown solid were obtained. 92% TOCAP by HPLC, overall yield from diphenylterephthalate 73%. m.p. 212°–215° C.

$-^1$NMR (200MHz, 2:1 DMSO-d$_6$:CDCL$_3$) $\delta$8.50 (t, 2H, J=5.5 Hz), 7.90 (s, 4H), 3.27 (q, 4H, J=6.0 Hz), 2.22 (t, 4H, J=7.2 Hz), 1.60–1.34 (m, 12H)

IR (Nujol):3320, 1715, 1705, 1630, 1540, 1465, 1320, 1295, 1280, 1235, 1160, 1100, 1015, 940, 865, 855, 730 cm$^{-1}$

EXAMPLE 5

A series of experiments were conducted to evaluate the effect of dimethylterephthalate concentration on the synthesis of TOCAP. These evaluations are reported in Table I.

TABLE I

| | Effect of Dimethylterephthalate Concentration in Methanol* | | | | | | |
|---|---|---|---|---|---|---|---|
| EXPERIMENT | DMT CONC. (M) | TIME TO PPT | RXN TIME | TOCAP YIELD | % PURITY | | |
| | | | | | TOCAP | MONO | TA |
| 1 | 0.13 | >24 h | 48 h | 40% | 64 | 28.7 | 1.0 |
| 2 | 0.25 | <16 h | 24 h | 48% | 67 | 27.1 | 1.1 |
| 3 | 0.50 | 0.75 h | 18 h** | 77% | 88.7 | 9.0 | 0.1 |
| 4 | 0.83 | 0.5 h | 3.5 h** | 65% | 87 | 5 | .03 |

*Conditions
3.0 equiv. sodium aminocaproate
0.2 equiv. sodium methoxide catalyst
**Reaction was stopped because mixture became unstirrable.

Using catalytic concentrations of sodium methoxide (0.2 molar equivalents relative to dimethyl terephthalate), conversion to TOCAP was maximized at a concentration of 0.50M. As the concentration of the reaction was increased, the reaction time decreased. At concentrations of 0.50M and 0.83M, the mixture became unstirrable and was stopped for this reason. Even at 0.25M, the product formed a thick layer on the outside of the flask, which on larger scale batches caused charring of the solid and did not allow for even heat distribution. The solubility of TOCAP salt is approximately 1.5 g/100 g at 60° C. The low solubility of the product, and the form of these particles, which are very fine and form a gel in methanol, required this reaction to be conducted under dilute conditions.

EXAMPLE 6

A series of experiments were conducted to determine the effect of pH in the work up of TOCAP generated from reactions in methanol. Table II provides results from this investigation.

TABLE II

| | Effect of Work-Up pH* | | | | |
|---|---|---|---|---|---|
| EXPERI-MENT | WORK-UP pH | % PURITY | | | TOCAP YIELD |
| | | TOCAP | MONO | TA | |
| | 24 Hour Reaction Time | | | | |
| 1 | pH 3 | 89.2 | 6.9 | 0.1 | 77% |
| 2 | pH 5 | 98.0 | 0.7 | 0.02 | 74% |
| 3 | pH 6 | 98.1 | 0.6 | 0.02 | 61% |
| | 4 Hour Reaction Time | | | | |
| 4 | pH 3 | 75.4 | 17.3 | 4.4 | 66% |

TABLE II-continued

Effect of Work-Up pH*

| EXPERIMENT | WORK-UP pH | % PURITY TOCAP | % PURITY MONO | % PURITY TA | TOCAP YIELD |
|---|---|---|---|---|---|
| 5 | pH 4 | 95.6 | 2.1 | 0.07 | 61% |

*Conditions: 0.25M, 2 equiv. NaOCH$_3$

The experiments in Table II were worked-up by pouring the methanol solution onto icewater to obtain a clear solution. Dilute sulfuric acid was then added to the methanol/water mixture until the desired pH was attained. For the 24 hour reactions, acidification to pH 3 gave product purity of 89%, whereas stopping the acidification at pH 5 or 6 gave a purity of 98%. However, there was a large loss in yield for the pH 6 acidification experiment. The differences were even more dramatic with a cruder product. For instance, when the reaction was stopped after 4 hours and acidified to pH 3, the purity decreased to 75%. Acidification to pH 4 greatly improved the purity, i.e. to 96%. It appears that the best balance of purity and yield is achieved between pH 4 and 5.

The foregoing description and Examples illustrate selected embodiments of the present invention. In light thereof, various modifications will be suggested to one skilled in the art, all of which are in the spirit and purview of this invention.

What is claimed is:

1. A process for the preparation of a bis(amidocarboxylic acid) having the formula:

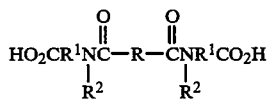

$$\text{HO}_2\text{CR}^1\overset{\text{O}}{\overset{\|}{\text{N}}}\text{C}-\text{R}-\overset{\text{O}}{\overset{\|}{\text{C}}}\text{NR}^1\text{CO}_2\text{H} \quad (I)$$
$$\qquad\quad\;\;|\qquad\qquad\quad\;|$$
$$\qquad\quad\;\text{R}^2\qquad\qquad\;\text{R}^2$$

wherein
R and R$^1$ are each independently a C$_1$–C$_{12}$ radical selected from the group consisting of alkylene, alkenylene, cycloalkylene, cycloalkenylene, arylene and phenylene radicals; and
R$^2$ is hydrogen or a C$_1$–C$_{12}$ radical selected from the group consisting of alkyl, alkenyl, cycloalkyl, cycloalkenyl, aryl and phenyl radicals;

the process comprising the steps of:
(i) charging a reactor with a reaction medium that includes a C$_1$–C$_8$ mono- or polyhydric alcohol as solvent, an ester and an aminocarboxylate compound, the ester having the formula:

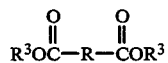

$$\text{R}^3\text{OC}-\text{R}-\text{COR}^3 \quad (II)$$

wherein R$^3$ is a C$_1$–C$_6$ radical selected from the group consisting of alkyl, haloalkyl, hydroxyalkyl and phenyl radicals, the aminocarboxylate compound being a salt formed from and selected from the group consisting of lactams having the formula:

and aminocarboxylic acids having the formula:

the ester and aminocarboxylate compound being present in a respective weight ratio of from about 1:1 to about 1:4;
(ii) reacting the ester with the aminocarboxylate compound; and
(iii) recovering the bis(amidocarboxylic acid) from the reaction medium.

2. A process according to claim 1 wherein the monohydric alcohol is selected from the group consisting of methanol, ethanol, isopropanol, n-propanol and phenol.

3. A process according to claim 1 wherein the polyhydric alcohol is selected from the group consisting of ethylene glycol, glycerol, propylene glycol, 1,4-butanediol and diethylene glycol.

4. A process according to claim 3 wherein the solvent is ethylene glycol.

5. A process according to claim 1 wherein the ester is dimethylterephthalate.

6. A process according to claim 1 wherein the ester is diphenylterephthalate.

7. A process according to claim 1 wherein the lactam is ε-caprolactam.

8. A process according to claim 1 wherein the aminocarboxylate compound is sodium 6-aminocaproate.

9. A process according to claim 6 wherein the alcohol is phenol.

10. A process according to claim 1, further comprising acidifying reaction products from step (ii) to a pH of no lower than 4, prior to separating the bis(amidocarboxylic acid) in step (iii).

11. A process according to claim 1 wherein the ester is present in a molar concentration prior to reaction under step (ii) at a level no higher than about 1 molar.

12. A process according to claim 1 wherein the bis(amidocarboxylic acid) is N,N'-terephthaloyl-di(6-aminocaproic acid).

* * * * *

UNITED STATES PATENT AND TRADEMARK OFFICE
CERTIFICATE OF CORRECTION

PATENT NO. : 5,393,902  
DATED : February 28, 1995  
INVENTOR(S) : Coope et al.

Page 1 of 2

It is certified that error appears in the above-indentified patent and that said Letters Patent is hereby corrected as shown below:

Column 3, lines 5-9; Column 4, lines 40-45 and Column 10, lines 6-12 change:

(III)

UNITED STATES PATENT AND TRADEMARK OFFICE
CERTIFICATE OF CORRECTION

PATENT NO. : 5,393,902

DATED : February 28, 1995

INVENTOR(S) : Coope et al.

Page 2 of 2

It is certified that error appears in the above-indentified patent and that said Letters Patent is hereby corrected as shown below:

to read:

--

 (III)

--

Signed and Sealed this

Ninth Day of May, 1995

Attest:

BRUCE LEHMAN

Attesting Officer     Commissioner of Patents and Trademarks